(12) United States Patent
Diamond

(10) Patent No.: US 6,518,308 B2
(45) Date of Patent: Feb. 11, 2003

(54) COMPOSITIONS FOR ADHESION PREVENTION

(76) Inventor: Michael P. Diamond, 45 Oxford Rd., Grosse Point, MI (US) 48236

( * ) Notice: Subject to any disclaimer, the term of this patent is extended or adjusted under 35 U.S.C. 154(b) by 0 days.

(21) Appl. No.: 10/012,711

(22) Filed: Nov. 16, 2001

(65) Prior Publication Data

US 2002/0068762 A1 Jun. 6, 2002

Related U.S. Application Data

(60) Provisional application No. 60/252,297, filed on Nov. 21, 2000.

(51) Int. Cl.⁷ .............................................. A61K 31/19
(52) U.S. Cl. ....................................... 514/557
(58) Field of Search ......................... 514/557

(56) References Cited

U.S. PATENT DOCUMENTS

| | | |
|---|---|---|
| 4,819,617 A | 4/1989 | Goldberg et al. |
| 4,886,787 A | 12/1989 | de Belder et al. |
| 6,011,017 A | 1/2000 | Marangos et al. |
| 6,211,217 B1 * | 4/2001 | Spinale et al. ............... 514/381 |
| 2002/0019419 A1 * | 2/2002 | de Laszlo et al. .......... 514/327 |

FOREIGN PATENT DOCUMENTS

| WO | WO 95/24929 | 9/1995 |
|---|---|---|
| WO | WO 97/03702 | 2/1997 |
| WO | WO 00/20642 | 4/2000 |

OTHER PUBLICATIONS

Chickering, D. et al. Poly(fumaric–co–sebacic) Microspheres as Oral Drug Delivery Systems, *Biotech. & Bioeng.* 52, 96–101 (1996).

Mathlowitz, E. et al. Biologically erodable microspheres as potential oral drug delivery systems. *Nature* 386, 410–414 (Mar. 27, 1997).

Sawhney, A. S. et al. Bioerodible Hydrogels Based on Photopolymerized Poly(ethylene glycol)–co–poly($\alpha$–hydroxy acid) Diacrylate Macromers. *Macromolecules* 26, 581–587 (1993).

Stacpoole, P. W. et al. Metabolic Effects of Dichloroacetate in Patients with Diabetes Mellitus and Hyperlipoproteinemia. *New England J. Med.* 8, 526–530 (Mar. 9, 1978).

Stacpoole, P. W. et al. Treatment of Lactic Acidosis with Dichloroacetate. *New England J. Med.* 309, 390–396 (Aug. 18, 1983).

Shagraw R.E. et al. Hepatic pyruvate deydrogenase activity in humans: Effect of cirrhosis, transplantation, and dichloroacetate. *Am. J. Physiology* 274 (Mar. 1998) from BIOSIS on ACS, Acc. No. 1998: 208437—ABSTRACT.

Walsh, F. et al. Dichloracetate reduces arterial lactate in patients with low cardiac output syndrome following cardiac surgery. *Anesthesiology* (*Hagerstown*) 89 (Sep. 1998) from BIOSIS on ACS, Acc. No. 1998: 466160—ABSTRACT.

* cited by examiner

*Primary Examiner*—William R. A. Jarvis
*Assistant Examiner*—Vickie Kim
(74) *Attorney, Agent, or Firm*—Ropes & Gray

(57) ABSTRACT

Compositions and methods for the prevention of adhesion development involve the administration of therapeutic formulations of a halogenated organic compound to a patient in need of treatment. The formulations can include suitable carriers for optimal administration.

6 Claims, No Drawings

COMPOSITIONS FOR ADHESION PREVENTION

This Application claims the benefit of No. 60/252,297, filed Nov. 21, 2000.

BACKGROUND OF THE INVENTION

It is well known that postoperative adhesions develop in the majority of patients following surgery. Adhesions can result in serious medical consequences and lifelong morbidity, including infertility, abdomino-pelvic pain, small bowel obstruction, and difficult reoperative procedures. Adhesions can manifest themselves shortly after the surgical procedure is performed, or many years thereafter, without any degree of predictability. Although adhesions are common in intraabdominal surgeries, adhesions can be a problem in virtually all types of surgeries. The haloorganic compounds of this invention, when formulated into pharmaceutical compositions, are useful in preventing or reducing the development of postoperative surgical adhesions, and therefore are of major clinical significance for the reduction of patient morbidity and mortality.

Postoperative surgical adhesions are generally believed to result from an injury or inflammation in the peritoneal cavity which produces a fibrous exudate. As a result of this exudate, the serosal tissue surfaces stick together. The fibrous exudate may be absorbed or invaded by fibroblasts to form a permanent fibrous adhesion.

Removal of fibrin before it is invaded by fibroblasts can prevent the development of permanent fibrous adhesions. Removal of fibrin occurs due to the fibrinolytic activity of the peritoneal cavity. Fibrinolytic activity can vary as a result of surgery, but it is absent from a peritoneal wound during the first 48 hours following surgery. However, there is a gradual increase in fibrinolytic activity after this time for up to eight (8) days when the peritoneum heals.

The mechanisms of peritoneal healing, and the alterations which result in postoperative adhesion development, are not well understood. Compositions which are currently approved by the U.S. FDA for use in the reduction of intraperitoneal adhesions theoretically serve as adhesion barriers that separate opposing, potentially adherable sites during the critical three to five day period of peritoneal repair.

Such compositions, including Intercede™, which is manufactured and sold by Johnson and Johnson, and Seprafilm™, which is manufactured and sold by Genzyme Corporation, are resorbable. i.e. reabsorbed in the surrounding tissue, and have been shown in clinical trials to reduce adhesions at the site where they are placed during a laparotomy. However, there is no clinical evidence that these compositions are of any benefit at sites within the patient removed form the site of application for the reduction of de novo adhesion formation, or for the reduction in adhesion reformation at such other sites. Similarly, there is no convincing clinical evidence that these materials are efficacious for surgical procedures performed by laproscopy, perhaps in part due to the difficulty in laproscopic placement of the material.

PCT published patent application WO 00/20642, published Apr. 13, 2000, discloses methods for the prevention of adhesion development by the administration of therapeutic formulations containing TIMP-1 antibodies to a patient. TIMP-1 is part of a family of inhibitors of metalloproteinase proteins, or TIMP's, which regulate the catalytic activity of matrix metalloproteinases (MMP's). The administration of antibodies to TIMP-1 to a patient is believed to alter the local levels of both TIMP-1 and MMP, and specifically to reduce the expression of TIMP-1, to thereby inhibit the development of adhesions.

Accordingly, there is perceived to be a need for an improved method for adhesion control and prevention which can be conveniently administered to a patient, and which is not restricted to the site of a particular surgical procedure. There is a particular need for such an, improved method which can also be used in connection with the rapidly growing field of laproscopic surgeries, and at sites throughout the body in addition to the abdominal cavity.

SUMMARY OF THE INVENTION

The present invention relates to methods for preventing or reducing the development of surgical adhesions, and compositions which can be used in such methods.

In one aspect, the invention includes a pharmaceutical formulation for preventing or reducing the development of surgical adhesions. The formulation contains, as an active ingredient, a halogenated organic compound of formula $CR_1OOR_2$, wherein $R_1$ is an alkyl group of 1 to 4 carbons, or a haloalkyl group of 1 to 4 carbons, and wherein $R_2$ is selected from the group consisting of hydrogen, halogen, lower alkyl and lower haloalkyl, provided that either $R_1$ or $R_2$ must contain at least one halogen. The pharmaceutical formulation can also include suitable pharmaceutically acceptable carriers and adjuvants, as well as other therapeutic compounds which assist in the prevention of adhesions. The term "pharmaceutically acceptable carrier" denotes a carrier substance that potentiates, and does not significantly diminish, the effect of the active agent in the body.

The terms "prevent" and "preventing" as used herein refer to inhibiting completely or partially a biological response, as well as inhibiting an increase in a biological response. For instance, prevention of adhesion development refers to partially or completely inhibiting adhesion formation and adhesion reformation, as well as inhibiting an increase in adhesion formation and adhesion reformation.

In a preferred embodiment, the halogenated compound of this invention is a halogenated acetic acid derivative, more preferably dichloroacetic acid or 2-chloropropionate. Prodrugs which form the halogenated compounds in the body can also be used, and are included within the scope of this invention. Additional modifications embraced by this invention include carriers which can be used to bind the halogenated compounds prior to administration, and which subsequently release the halogenated compounds in the body in active form. Suitable biocompatible carriers are well known to those skilled in the art.

Typically, the pharmaceutical composition of the invention contains from about 1% to about 50% active ingredient, and preferably from about 2% to about 10% active ingredient. Human dosages in the range of from about 10 mg/kg to about 100 mg/kg can be used depending on the severity of the particular condition and the treatment protocol.

The pharmaceutical composition can be delivered to the subject by any route known in the art. For instance, the pharmaceutical composition can be administered systemically, such as orally or parenterally, or it may be administered locally. The pharmaceutical composition can also be delivered in a sustained release device. Alternatively, the pharmaceutical composition can be administered with an anti-adhesion adjuvant to obtain the benefits of a barrier compound and the adhesion prevention composition. The adjuvant may be used in the form of a gel, liquid or a solid membrane. Typical anti-adhesion adjuvants which are useful in this invention include commercial products such as Intercede® and Seprafilm®.

In another aspect, this invention includes a method for preventing or reducing the development of surgical adhesions by treating a patient at risk of developing such adhesions with a therapeutic formulation containing, as an active ingredient, a halogenated organic compound of formula $CR_1OOR_2$, wherein $R_1$ is selected from the group consisting of lower alkyl groups (of 1 to 4 carbons), or lower haloalkyl groups, and wherein $R_2$ is selected from the group consisting of hydrogen, halogen, lower alkyl and lower haloalkyl, provided that either $R_1$ or $R_2$ must contain at least one halogen atom.

Although it is most common to use the pharmaceutical compositions of this invention for peritoneal surgery, the type of surgery in which the product is used may be any type where there is a risk of developing surgical adhesions associated with the surgery. In some embodiments, the subject can undergo a surgery selected from the group consisting of abdominal surgery, gynecological surgery, cardiac surgery, back surgery, neurosurgery, ligament and tendon surgery, and ophthalmic surgery.

DETAILED DESCRIPTION OF THE INVENTION

This invention is based, in part, on the discovery that the development of adhesions is a response mechanism by the subject to a disruption in the preexisting vasculature supplying blood to the injured tissue present in the subject. Adhesions essentially represent a mechanism for resupplying oxygen nutrients to the injured tissue to promote healing.

Tissue which is injured as a result of a pathological process, or by a surgical procedure undertaken to treat a pathology, experience a disruption in the vasculature, resulting in the delivery of less oxygen and nutrients to the tissue. This, in turn, causes a buildup of metabolic wastes due to the impairment of the normal mechanisms of waste removal.

Tissue normally utilize an aerobic metabolism in which energy is derived by the cells from the oxidation of metabolic intermediates and oxygen to form carbon dioxide. This metabolic reaction is the primary route by which cells are able to derive the maximum number of ATP (energy) molecules possible by passing all carbon sources being metabolized from pyruvate through the Kreb's (tricarboxylic acid) cycle. However, if the amount of oxygen is limited by the disruption of the vasculature delivering blood to the injured tissue, oxidative metabolism is hindered or rendered unable to occur. Such injury may be due, for instance, to a pathological process, to the cutting of blood vessels, to tying off vessels during surgery, or to the use of electrosurgical energy for sealing blood vessels. In such situations, the injured tissue produces markedly fewer ATP molecules. In addition, pyruvate is less likely to enter the Kreb's cycle, but rather is converted into lactic acid which will build up in the affected, anoxic (hypoxic) tissues.

It is hypothesized that the body is able to sense the anoxia/hypoxia in the injured tissues, and in response, produces adhesions from adjacent tissue which subsequently become vascularized as a mechanism for resupplying oxygen and other nutrients to the tissue. This results in the attachment of tissues at non-physiologic locations, with the potential of untoward adverse clinical consequences.

While not intending to be bound by any particular theory, it is believed that the pharmaceutical compositions of this invention are effective in reducing the incidence of postoperative adhesions by stimulating the activity of the enzyme pyruvate dehydrogenase, so that virtually all pyruvate enters the Kreb's cycle. This results in maximal ATP production, while simultaneously reducing the conversion of pyruvate into lactic acid. The tissue thus becomes less anoxic/hypoxic, and there is less stimulus to form an adhesion. The pharmaceutical formulation is advantageously administered to a subject prior to or during surgery, in order to be present during the peritoneal healing, and preferably for approximately three to five days following surgery.

The halogenated organic compounds of this invention include compounds of the general formula $CR_1OOR_2$, wherein $R_1$ is selected from the group consisting of lower alkyl groups or lower haloalkyl groups, and wherein $R_2$ is selected from the group consisting of hydrogen, halogen, lower alkyl groups and lower haloalkyl groups, provided that either $R_1$, or $R_2$ must contain at least one halogen atom. The term "lower," in the context of this invention, when used to modify "alkyl" or "haloalkyl", includes $C_1$ to $C_4$ alkyls or haloalkyls. Suitable halogens can include chloro, bromo, iodo and fluoro groups, although chloro is preferred. $R_1$ is preferably a chloromethyl group, and $R_2$ is preferably hydrogen. Preferably, the halogenated compounds use in this invention are dichloroacetic acid or 2-chloropropionate.

The halogenated organic compounds of this invention are well known compounds which are available from commercial sources. Alternatively, the halogenated organic compounds can be synthesized using techniques which are well known in the art to synthetic organic chemists. These compounds are biocompatible and have been found useful in unrelated therapeutic uses, such as, for instance, the treatment of severe lactic acidosis associated with septic shock, P. W. Stacpoole et al., *The New England Journal of Medicine*, 7, pages 390–396 (1983); and the treatment of diabetes mellitus and hyperlipoproteinemia, Stacpoole et al., *The New England Journal of Medicine*, 8, pages 526–530 (1978).

The halogenated compounds are administered to a subject in a pharmaceutical formulation to induce protection against postoperative surgical adhesion development associated with many common types of surgery. Adhesions are a common complication of surgery that involve abnormal union of tissue surfaces, often occurring during the healing process of injured cells, tissues and organs. Postoperative surgical adhesions are a major complication of abdominal, pelvic, gynecologic, cardiothoracic, orthopedic and neurosurgeries. Adhesions may result after a trauma sustained by the body, such as a surgery or a wound, and may develop in a variety of areas in the body.

The type and degree of damage caused by adhesions is variable, ranging from life-threatening damage, as in the intestines due to ablockage, to extremely disabling damage, as in tendons or spinal cord, to chronic pain and infertility in the pelvic cavity, to the obstruction of further surgery in the pericardium. Adhesions that form in relation to intestinal surgery, e.g., bowel resection, hernia repair, etc., may cause obstruction of the intestine. Adhesions that form near a bone fracture site may reduce or hinder the normal movement in the area of repair by restricting the natural movement of tendons over the adjacent bone. Adhesions may also form in the vicinity of nerves and disrupt nerve transmissions with a resultant diminution of sensory or motor function. Postoperative development of pelvic adhesions remains a serious problem in patients undergoing gynecological surgery and is a principal cause of infertility. Postoperative adhesion development can necessitate difficult reoperations and an increase in injuries during subsequent surgeries. In general, the most common causes of pelvic adhesions in women are prior surgery, endometriosis and pelvic inflammatory disease.

Current clinical methods directed toward reducing the development of postoperative surgical adhesions generally rely on placement of a film or gel directly at the operative site, with the intention of creating a physical barrier between surfaces likely to become involved in adhesion development. These methods remain cumbersome for the surgeon to use.

Highly concentrated solutions of a number of polymers have been used to coat the surgical area before and during surgery so as to minimize tissue drying and to act as a cushion to prevent some of the manipulative trauma. Examples of these techniques are described in U.S. Pat. No. 4,819,617 to Goldberg et al. and U.S. Pat. No. 4,886,787 to De Belder et al. Among the materials used are polyvinylpyrrolidone (PVP), dextrans, hyaluronic acid, carboxymethylcelluloses, and a number of other polymers such as protein or polypeptide solutions. These materials do not entirely eliminate adhesions, but rather reduce the incidence of adhesion development. The compounds of this invention are believed to be significantly more effective for adhesion reduction than the barrier materials of the prior art.

It has now been discovered, according to the invention, that the administration of the compounds of the invention, locally or systemically, can induce protection against postoperative surgical adhesion development.

Thus, the compositions of the invention are useful for treating or preventing adhesions that form at a site and that have potential or actual deleterious effects. These include primary and secondary adhesions in the following sites: in the abdominal cavity, including intestine to intestine, and intestine to peritoneum; in the pelvic cavity, including adhesions of the uterus, ovaries or fallopian tubes to other structures including each other and the pelvic wall; in tendons and their support structures, including tendon to pulley or to synovium; in the repair of nerve sheaths; in the repair of the spinal column or disks; in the pericardium; in the treatment of joints for inflammation, and to prevent pannus formation; in the extraocular muscle, to prevent adhesions from limiting the field of vision; and in any situation in which adhesions form which can impair the function or cause pain.

The prevention of postoperative surgical adhesion development in a subject includes prophylactic treatment to prevent adhesion development following planned surgical procedures, as well as following emergency operations. In addition to the surgical procedures described above, elective surgeries include the following intraabdominal surgeries: right hemicolectomy; left hemicolectomy; sigmoid colectomy; subtotal colectomy; total colectomy; laparoscopic or open cholecystectomy; gastrectomy; pancreatectomy; splenectomy; liver, pancreas, small bowel, or kidney transplantation; lysis of adhesions; cesarean sections and other pelvic procedures, uterine surgery, etc. Emergency intraabdominal surgeries include those surgeries used to correct the following conditions: perforated ulcer (duodenal or gastric); perforated diverticulitis; obstructive diverticulitis; bowel obstruction; perforated appendicitis; blunt abdominal trauma; penetrating abdominal trauma; ruptured abdominal aortic aneurysm, cardiac surgeries, open and endoscopic orthopedic surgeries, neurosurgeries, gynecologic and pelvic surgeries, and surgeries to correct wound infections.

The compounds of the invention are administered in an effective amount for inducing protection against postoperative surgical adhesion development. An effective amount for inducing protection against postoperative surgical adhesion development as used herein is that amount of pharmaceutical composition that will, alone or together with further doses or additional therapeutic compounds, inhibit or prevent the development of postoperative surgical adhesions.

The preparations of the invention when administered "in conjunction with" a surgical procedure, are administered close enough in time with the surgery or trauma that predispose the host to adhesion development, so that a protective effect against the particular disorder is obtained. The preparations may be administered long before the surgery, e.g., in the case of elective surgery (i.e., weeks or even months), preferably with booster administrations closer in time to (and even after) the surgery. Particularly in emergency situations, the preparations may be administered immediately before (minutes to hours) and/or after the surgery. It is important only that the preparation be administered close enough in time so as to enhance the subject's response against adhesions, thereby increasing the chances of a successful host response and reducing the likelihood of adhesion development.

The present invention provides pharmaceutical compositions for medical use, which in some aspects comprise the compounds of the invention together with one or more pharmaceutically acceptable carriers and optionally other therapeutic ingredients. Thus the invention may also include pharmaceutical compositions in combination with an anti-infectious agent such as an antibacterial or anti-viral agent, an anti-inflammatory agent, an antibiotic, or other therapeutic agent, and a pharmaceutically acceptable carrier. The pharmaceutical compositions useful in the invention may be delivered separately with the other therapeutic agents, or in the form of therapeutic cocktails. A therapeutic cocktail includes a mixture of the pharmaceutical compositions of the invention and another therapeutic agent. In this embodiment, a common administration vehicle (e.g. tablet, implant, injectable solution, etc.) contains both the pharmaceutical composition and another therapeutic agent. Alternatively, the other therapeutic can be separately dosed if desired.

The precise amount of the therapeutic agent used in combination with the pharmaceutical compositions of the invention depends upon a variety of factors, including the particular pharmaceutical composition selected, the dose and dose-timing selected, the mode of administration, the nature of any surgical or medical procedure contemplated, and the characteristics of the subject. Where local administration is carried out, it will be understood that very small amounts may be required (nanograms and possibly picograms). The precise amounts selected can be determined without undue experimentation, particularly since a threshold amount is any amount which will favorably enhance the response.

Multiple doses of the pharmaceutical compositions of the invention are also contemplated. For instance, when being administered in conjunction with a surgical procedure, the compounds of the invention can be administered in multiple doses over a three week to one day period preceding surgery. Further, doses may be administered post surgery as well. Any regimen that prevents or retards the development of adhesions may be used, although optimum doses and dosing regimens are those that would not only inhibit the development of adhesion formation, but also would result in protection against adhesion development. Desired time intervals for the delivery of multiple doses of a particular pharmaceutical composition can be determined by one of ordinary skill in the art employing no more than routine experimentation.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The pharmaceutical composition may be administered per se (neat) or in the form of a pharmaceutically acceptable salt. When used in medicinal applications, the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid or its salt (1–2% w/v); citric acid or its salt (1–3% w/v); boric acid or its salt (0.5–2.5% w/v); succinic acid; and phosphoric acid or its salt (0.8–2% w/v). Suitable preservatives include benzalkonium chloride (0.003–0.03% w/v); chlorobutanol (0.3–0.9% w/v); parabens (0.01–0.25% w/v) and thimerosal (0.004–0.02% w/v).

The pharmaceutical compositions of the invention contain an effective amount of a pharmaceutical composition optionally included in a pharmaceutically acceptable carrier. The term "pharmaceutically acceptable carrier" means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application of the composition. The components of the pharmaceutical compositions also are capable of being commingled with the pharmaceutical compositions of the present invention, and with each other, in a manner such that there is no interaction which would substantially impair the desired pharmaceutical efficiency.

Compositions suitable for parenteral administration conveniently comprise sterile aqueous preparations, which can be isotonic with the blood of the recipient. Among the acceptable vehicles and solvents are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for subcutaneous, intramuscular, intraperitoneal or intravenous administrations may be found in Remington's Pharmaceutical Sciences, Mack Publishing Company, Easton, Pa.

The pharmaceutical compositions useful in the invention may be delivered in mixtures of more than one pharmaceutical composition. A mixture may consist of several pharmaceutical compositions.

A variety of administration routes are available. The particular mode selected will depend, of course, upon the particular pharmaceutical composition selected, the particular condition being treated, and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration include parenteral, injection, infusion, deposition, implantation, anal or vaginal supposition, oral ingestion, inhalation, topical administration. Injections can be intravenous, intradermal, subcutaneous, intramuscular, or interperitoneal. For example, the pharmaceutical composition can be injected directly into the surgical site for the prevention of adhesions. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the pharmaceutical composition with an aerosol in an inhaler, either alone or attached to a carrier that can be absorbed. For systemic administration, it may be preferred that the pharmaceutical composition is encapsulated in liposomes. The term "parenteral" includes subcutaneous injections, intravenous, intramuscular, intraperitoneal, and intrasternal injection or infusion techniques.

In certain preferred embodiments of the invention, the administration can be designed so as to result in sequential exposure to the pharmaceutical composition over some period of time, e.g., hours, days, weeks, months or years. This can be accomplished by repeated administrations of the pharmaceutical composition, by one of the methods described above, or alternatively, by a sustained-release delivery system in which the pharmaceutical composition is delivered to the subject for a prolonged period without repeated administrations. By sustained-release delivery system, it is meant that total release of the pharmaceutical composition does not occur immediately upon administration, but rather is delayed for some period of time. Release can occur in bursts or it can occur gradually and continuously. Administration of such a system can be, e.g., by long-lasting oral dosage forms, bolus injections, transdermal patches, and subcutaneous implants.

Examples of systems in which release occurs in bursts includes, e.g., systems in which the pharmaceutical composition is entrapped in liposomes which are encapsulated in a polymer matrix, the liposomes being sensitive to specific stimuli, e.g., temperature, pH, light or a degrading enzyme and systems in which the pharmaceutical composition is encapsulated by an ionically-coated microcapsule with a microcapsule core degrading enzyme. Examples of systems in which release of the pharmaceutical composition is gradual and continuous include, e.g., erosional systems in which the pharmaceutical, composition is contained in a form within a matrix, and effusional systems in which the pharmaceutical composition permeates at a controlled rate, e.g., through a polymer. Such sustained release systems can be e.g., in the form of pellets, or capsules.

In one particular embodiment, the preferred sustained release device is a biocompatible microparticle or microencapsulated product or implant that is suitable for implantation or administration to the mammalian recipient. Exemplary bioerodible implants that are useful in accordance with this method are described in PCT International application no. PCT/US/03307 (Publication No. WO 95/24929, entitled "Polymeric Gene Delivery System.") The polymeric matrix preferably is in the form of a microparticle such as a microsphere (wherein the pharmaceutical composition is dispersed throughout a solid polymeric matrix) or a microcapsule (wherein the pharmaceutical composition is stored in the core of a polymeric shell). Other forms of the polymeric matrix for containing the pharmaceutical composition include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue. The polymeric matrix composition can be selected to have both favorable degradation rates and also to be formed of a material which is bioadhesive, to further increase the effectiveness of transfer when the matrix is administered to a mucosal surface. The matrix composition also can be selected not to degrade, but rather to release by diffusion over an extended period of time. The biocompatible microsphere may be suitable for oral delivery. Such microspheres are disclosed in Chickering et al., Biotech. And Bioeng., (1996) 52:96–101 and Mathiowitz et al., *Nature*, (1997) 386:410–414 and PCT Patent Application No. WO97/03702.

Both non-biodegradable and biodegradable polymeric matrices can be used to deliver the pharmaceutical compositions to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water, and further optionally is cross-linked with multi-valent ions or other polymers.

Bioadhesive polymers of particular interest include bio-erodible hydrogels described by H. S. Sawhney, C. P. Pathak and J. A. Hubell in *Macromolecules*, (1993) 26:581–587, the teachings of which are incorporated herein by reference, casein, gelatin, glutin, polyanhydrides, polyacrylic acid, alginate, chitosan, poly(methyl methacrylates), poly(ethyl methacrylates), poly(butylmethacrylate), polyhyaluronic acids, poly(isobutyl Miiiethaerylate), poly (hexylmethacrylate), poly(isodecyl methacrylate), poly (lauryl methacrylate), poly(phenyl)methacrylate), poly (methyl acrylate), poly(isopropyl acrylate), poly(isobutyl acrylate), and poly(octadecyl acrylate).

Other sustained release delivery systems useful according to the invention include, but are not limited to, fatty acids and a medicinal pump. Preferably the fatty acids are $C_9$–$C_{20}$ fatty acids.

The compositions may conveniently be presented in unit dosage form and may be prepared by any of the methods well known in the art of pharmacy. Such methods include the step of bringing the pharmaceutical composition into association with a carrier which constitutes one or more accessory ingredients. In general, the compositions are prepared by uniformly and intimately bringing the pharmaceutical composition into association with a liquid carrier, a finely divided solid carrier, or both, and then, if necessary, shaping the product. The pharmaceutical composition may be stored in a lyophilized condition.

The pharmaceutical compositions can be suspended in a liquid, e.g., in dissolved form or colloidal form. The liquid can be a solvent, partial solvent, or non-solvent. In many cases, water or an organic liquid can be used.

The pharmaceutical compositions are administered to the subject in a therapeutically-effective amount. By therapeutically-effective amount it is meant that amount which is capable of at least partially preventing, reversing, reducing, decreasing, ameliorating, or otherwise suppressing adhesions. A therapeutically-effective amount can be determined on an individual basis and is based, at least in part, on consideration of the age, sex, size, and health of the subject; the type of pharmaceutical composition used, the type of delivery system used; the time of administration; and whether a single, multiple, or controlled-release dose regimen is employed. A therapeutically-effective amount can be determined by one of ordinary skill in the art employing such factors and using no more than routine experimentation.

The dosage concentration of the pharmaceutical composition actually administered is dependent, at least in part, upon the final concentration of the pharmaceutical composition that is desired at the site of action, the method of administration, the efficacy of the particular pharmaceutical composition, the longevity of the particular pharmaceutical composition, and the timing of administration. Preferably, the dosage form is such that it does not substantially deleteriously affect the subject. The dosage can be determined by one of ordinary skill in the art employing such factors and using no more than routine experimentation.

The term "subject," as used herein, means a human or non-human mammal, including but not limited to, a dog, cat, horse, cow, pig, sheep, goat, primate, rat, and mouse.

EXAMPLES

An animal adhesion study to evaluate the effectiveness of the pharmaceutical compositions described previously is conducted using a standardized animal model, such as a model of cecal abrasion in the rat or an oravian bisection in the rabbit.

The animals undergo lesioning by a surgeon unaware of group assignment, with necropsy performed one to two weeks later as is standard for that particular animal model.

The animals are randomized in a placebo control group and a group using dichloroacetic acid. The treatment begins preoperatively, and continues for five days after surgery. Dichloroacetic acid is administered by intravenous injection, or by slow release from a delivery agent, and is left in the peritoneal cavity following surgery. The maintenance of adequate amounts of dichloroacetic acid can be monitored by the measurement of serum alanine and lactate, which is reduced in the presence of dichloroacetic acid. Necropsy is performed on the animals, and adhesions are scored. Studies are completed on a total of 30 animals in each group in at least three settings.

Similarly, cell cultures using human mesothelial cells or human fibroblasts are cultured under hypoxic conditions in the presence and absence of dichloroacetic acid. The production of inflammatory cytokines and growth factors is measured, and found to be reduced in the presence of dichloroacetic acid. These growth factors, such as IL-1 and TGF-$\beta$, are believed to be associated with adhesion development.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

What is claimed is:

1. A method for preventing or reducing the development of surgical adhesions in a subject comprising treating a subject at risk of developing such adhesions with an effective amount of a therapeutic formulation containing, as an active ingredient, a halogenated organic compound of formula $CR_1OOR_2$, wherein $R_1$ is a lower alkyl or a lower haloalkyl, and wherein $R_2$ is selected from the group consisting of hydrogen, halogen, lower alkyl and lower haloalkyl, provided that either $R_1$ or $R_2$ must contain at least one halogen.

2. The method of claim 1 wherein the halogenated organic compound is an acetic acid derivative.

3. The method of claim 2 wherein the halogenated organic compound is dichloroacetic acid.

4. The method of claim 2 wherein the halogenated organic compound is 2-chloropropionate.

5. The method of claim 1 wherein the halogen is chlorine.

6. The method of claim 1 wherein the lower alkyl is methyl and the lower haloalkyl is halomethyl.

* * * * *